(12) United States Patent
Smiley

(10) Patent No.: US 6,323,156 B1
(45) Date of Patent: Nov. 27, 2001

(54) METHOD OF USING AMMONIUM FATTY ACID SALTS AS NON-SELECTIVE HERBICIDES

(75) Inventor: Robert A. Smiley, Wilmington, DE (US)

(73) Assignee: Falcon Lab LLC, Wilmington, DE (US)

( * ) Notice: Subject to any disclaimer, the term of this patent is extended or adjusted under 35 U.S.C. 154(b) by 0 days.

(21) Appl. No.: 09/560,664

(22) Filed: Apr. 27, 2000

(51) Int. Cl.⁷ ..................................................... A01N 37/00
(52) U.S. Cl. .............................................................. 504/320
(58) Field of Search .................................. 504/320

(56) References Cited

U.S. PATENT DOCUMENTS 5,919,733 * 7/1999 Sedun et al. ........................ 504/320

* cited by examiner

*Primary Examiner*—Alton Pryor
(74) *Attorney, Agent, or Firm*—Locke Liddell & Sapp LLP

(57) ABSTRACT

A method for controlling undesired vegetation that comprises contacting the vegetation with a herbicidally effective amount of a composition containing the compound of the formula $R_1COO^-X^+$ wherein $R_1$ is a $C_6$ to $C_{19}$ hydrocarbyl group optionally substituted with one or more hydroxyl or $C_1$–$C_5$ hydrocarbyl groups, and X is ammonium.

20 Claims, No Drawings

METHOD OF USING AMMONIUM FATTY ACID SALTS AS NON-SELECTIVE HERBICIDES

FIELD OF THE INVENTION

The present invention relates to the use of ammonium salts of fatty acids as non-selective herbicides to destroy the growth of plants.

BACKGROUND OF THE INVENTION

There are two major categories of herbicides to treat growing weeds—selective and non-selective. Selective herbicides only kill selected weeds such as broad leafed plants like dandelion, an example being the well-known herbicide 2,4-D. The non-selective herbicides kill all weeds. Commercially known non-selective herbicides include glyphosate (such as ROUNDUP®) and paraquat. Paraquat is a known hazardous material. Roundup often has a higher than desired kill time. Non-hazardous non-selective herbicides exhibiting decreased kill time are desired.

It is therefore a principal object of this invention to provide non-hazardous non-selective herbicides having low kill time for use on unwanted vegetation.

SUMMARY OF THE INVENTION

Vegetation may be killed by application of a composition of the formula:

$$R_1COO^-X^+ \qquad (I)$$

wherein $R_1$ is a $C_6$ to $C_{19}$ hydrocarbyl group and X is ammonium ($NH_4^+$). In the formula (I), any of the hydrogen on $R_1$ may be substituted with one or more hydroxyl or $C_1$–$C_5$ hydrocarbyl group, such as an alkyl group. The herbicidal composition of the invention contains essentially no free fatty acid content. Such compounds have been found to act as "non-selective" herbicides.

The invention relates to a method for killing unwanted vegetation, by applying to the locus of the unwanted vegetation a herbicide of formula (I). The composition may be applied as an aqueous solution and may further contain a surfactant. Since the mode of action appears to be through the leaves of the vegetation, there is little, if any, residual herbicidal effect in the ground. Thus, it is possible to grow desirable plants adjacent to and around the treated area.

DETAILED DESCRIPTION OF PREFERRED EMBODIMENTS

Unwanted vegetation may be killed by wetting the locus of the vegetation with a composition represented by the formula:

$$R_1COO^-X^+ \qquad (I)$$

wherein $R_1$ is a saturated or unsaturated $C_6$ to $C_{19}$ hydrocarbyl (preferably a $C_7$ to $C_{11}$ hydrocarbyl), or an epoxide or cycloproparie thereof, X is ammonium, ($NH_4$), and any of the hydrogen on $R_1$ may be substituted with one or more hydroxyl or $C_1$–$C_5$ hydrocarbyl groups. This herbicidal composition contains less than 0.5 wt. % free fatty acids. More preferred, the herbicidal composition of the invention contains less than 0.1 wt. % free fatty acids. In a most preferred embodiment, the herbicidal composition of the invention contains essentially no free fatty acids. The composition of the invention may further contain a diluent.

Any solvent in which the herbicide is soluble may be employed as a diluent. As a post-emergent, the herbicides of the invention are preferably applied to the locus of the unwanted vegetation as an aqueous solution.

The method of the invention may be used to control established vegetation in the vicinity of a seeded crop or in a weed concentrate area by contacting the foliage of the unwanted vegetation with the herbicidal composition. The herbicidal activity of such herbicidal compositions rapidly dissipates in the unwanted vegetation upon contact.

The herbicide is applied as a solution to the locus of the unwanted vegetation in effective amounts. Typically, the herbicide is applied as an aqueous solution wherein the amount of herbicide in the formulation is between about 3 to about 17, weight percent, preferably about 5 to about 15, weight percent, more preferably for some applications from about 5 to about 10, weight percent and for some other applications from about 10 to about 15, weight percent.

The herbicides of the invention exhibit several advantages not previously seen with other commercial herbicides. These advantages include:

More Rapid Kill Time.

Vegetation usually starts to die within an hour after receiving a single application. Typically unwanted vegetation is dead in less than 24 hours. Some readily obtainable herbicides require at least seven days. Further, herbicides evidencing quicker kill times in the prior art are highly toxic.

Based on Naturally Occurring Compounds.

Suitable herbicides for use in the invention include several based on acids found in nature. No commercially known water soluble herbicides are based on naturally occurring compounds.

Action is Through the Leaves.

In light of the quick kill time of the herbicidal compositions of the invention, reseeding can take place immediately. Most commercial herbicides must be allowed to degrade before reseeding.

Non-toxic and Biodegradable.

Herbicides within the invention are non-toxic and further are biodegradable. Most commercial herbicides are hazardous to apply.

Low Cost.

The herbicides of the invention are relatively low in cost.

Easy Transportation.

Unlike most commercial herbicides which as liquids must be shipped in containers requiring special disposal methods, the herbicides of the invention are water soluble solids and thus may be shipped in readily disposable containers. Upon reaching their desired location, the solid herbicide may be prepared into solutions at their requisite strength. Alternatively, the herbicides of the invention may be shipped as liquid compositions.

The herbicidal composition of the invention is contacted with the foliage of the unwanted vegetation by spraying or otherwise distributing the composition onto the foliage. Leaves of vegetation sprayed with herbicidal compositions of the invention usually start to shrivel or turn brown within hours after application. Necrosis is evident, usually in 24 hours. In the case of smaller weeds such as dandelions, chickweed and other common lawn weeds, the roots of the plants also shrivel and turn brown or black within 24 hours.

Spraying is a preferred method of wetting the leaves. A light spray is usually sufficient to kill the plant at ambient temperatures above 20° C. without any additional treatment. Herbicidal effectiveness generally increases with temperature.

Weeds and grasses which have been killed by use of the herbicidal composition of the invention include quack grass, buttercup, common cinquefoil, multi flora rose, common yellow woodsorrel, prostrate spurge, poison ivy, poison hemlock, common speedwell, broadleaf plantain, Japanese honeysuckle, dandelion, wild violet, Bermuda grass, nutsedge, wild garlic, knotweed, red sorrel, lambs quarters, pokeweed, carpetweed, crabgrass, buckhorn plantain, nimblewill or common chickweed.

The following examples will illustrate the practice of the present invention in its preferred embodiments. Other embodiments within the scope of the claims herein will be apparent to one skilled in the art from consideration of the specification and practice of the invention as disclosed herein. It is intended that the specification, together with the examples, be considered exemplary only, with the scope and spirit of the invention being indicated by the claims which follow.

EXAMPLE 1

A 12 liter round bottom kettle equipped with stirrer and capable of being cooled was charged with 1218.8 gm. (7.7 mole) of pelargonic acid and 3440 ml. of deionized water. To this was fed with stirring 910.7 gm. 30% ammonium hydroxide. The temperature was maintained below 30° C. by cooling and adjusting the feed rate. The mixture became very thick and difficult to stir when approximately 15% of the total ammonium hydroxide had been added. To get better stirring, 2016 ml. more deionized water was added for a total of 5456 ml. When approximately 65% of the ammonium hydroxide was added, the solution turned crystal clear and remained so until all the ingredients were mixed. The final water white solution contained 17% ammonium pelargonate. Isolated anhydrous ammonium pelargonate from this solution is a soft, white, crystalline solid melting at 62° C. Ammonium pelargonate is extremely water soluble but is insoluble in acetone.

EXAMPLE 2

Jimson weed, soybean, common ragweed and annual grass (combination of annual bluegrass and fall panicum) were grown in 12 inch by 12 inch flats in a greenhouse maintained at 80° F. with supplemental lighting used to extend daylength to 16 hrs. Flats were watered as needed. When the plants were 3–6 inches high they were sprayed with a solution of 5% ammonium pelargonate solution prepared by dilution of a 17% solution with the required amount of water. The spraying was done in a spray chamber with a track mounted sprayer adjusted to spray at a rate of 50 gallon/acre. The control (degree of injury) obtained was Jimson weed (85%), soybean (75%) common ragweed (30%) while annual grass control was less than 10%.

EXAMPLE 3

Using the same procedure as set forth in Example 2, the flats were seeded with velvetleaf, annual morning glory, common ragweed and crabgrass. After growth some flats were treated with 5% ammonium pelargonate solution while others were sprayed with 10% ammonium pelargonate in the spray chamber at the same 50 gallon/acre rate. There was only a slight difference in the control ate between the two concentrations. At the 10% concentration, velvetleaf control was 90%, morning glory was 90%, common ragweed was 85% and crabgrass was 70%.

EXAMPLE 4

The same mixture used in Example 1 was sprayed on all of the leaves of larger plants including poison hemlock, Japanese honeysuckle, poison ivy, multiflora rose, tall buttercup, pokeweed, ragweed, wild grape and lambsquarters. All treated plants died within 24–48 hours. There was no re-growth.

EXAMPLE 5

The leaves of tree suckers sprouting from the stumps of a variety of sawed off trees were sprayed with the mixture used in Example 1. The sprouts all died within 24–48 hours and no new growth from the stumps occurred.

EXAMPLE 6

Dilute ammonium hydroxide was added to 125 g. of pelargonic acid until the pH of the resulting solution was 7 as indicated by pH paper. Enough water was added to bring the total solution to 2 liters. This 6.9% neutral solution of ammonium pelargonate was sprayed from a hand sprayer on dandelion, moneywort, Japanese honeysuckle, star of Bethlehem and henbit. Damage to the plants was evident within 4 hours as evidenced by wilting and/or change of color. The treated dandelion was dead within 12 hours. The rest were dead within 24–36 hours. This solution foamed on contact with the plant leaves.

EXAMPLE 7

The following weeds growing in the wild were treated with a 10% water solution of ammonium pelargonate: common evening primrose, Japanese honeysuckle, multiflora rose, common chickweed, henbit, wild onion, hairy bitter cress, dandelion and plantain. Treatment consisted of wetting the leaves of the plants with a hand sprayer. Damage was apparent on all plants within 12 hrs as evidenced by wilting and discoloration. The treated plants were all dead within 36–48 hours.

EXAMPLE 8–9

Large crabgrass, giant foxtail, jimsonweed, velvetleaf and annual morning-glory were seeded into 12 inch by 12 inch flats filled with potting soil maintained in a greenhouse of 80° F. Supplemental lighting was used to extend daylength to 16 hours. The flats were watered as needed. Three weeks after planting, when the grasses were about 3 inches tall and the broadleaves were 2 to 4 inches tall, individual flats were treated with 5, 7.5, 10 and 15% solutions of ammonium pelargonate. For comparison purposes, other flats were treated with the same concentrations of pelargonic acid prepared from a commercially available herbicide sold under the tradename "Scythe" by Dow AgraSciences. The solutions were applied with a track-mounted sprayer in a spray booth at the rate of 50 gal./acre.

Ammonium pelargonate application resulted in plant injury within hours of application. Symptoms were typically water-soaked lesions that quickly resulted in dead tissue. Maximum injury symptoms were observed in the first week after treatment. With morning-glory, all concentrations gave the same control of 70%. However, with jimson weed there was a rate response with increasing rates giving increased control. Velvetleaf control was better at the 10 and 15% rates than at the 5 and 7.5% rates.

In relation to pelargonic acid, ammonium pelargonate was better than the commercial "Scythe" formulation. Lower concentrations of ammonium pelargonate gave better jimsonweed control than "Scythe" at higher concentration. At equal concentrations, ammonium pelargonate gave better control of velvetleaf and morning-glory than "Scythe", particularly at one week after treatment.

COMPARATIVE

EXAMPLE 10

The same variety of weeds set forth in Example 7 were treated with a 10% solution of potassium pelargonate made by neutralizing 80 gm. Pelargonic acid in 200 ml. water with 50% aqueous potassium hydroxide to a pH of 7 as indicated by pH paper followed by dilution with water to 1 liter of solution. None of the weeds were affected by the potassium pelargonate solution even after a week. Thus, ammonium pelargonate has herbicidal properties while the potassium salts has none.

What is claimed is:

1. A method for the prevention or elimination of undesired vegetation which comprises applying to the vegetation a herbicidally effective amount of an aqueous solution which contains, as the active ingredient, a salt represented by the formula:

$$R_1COO^-X^+ \qquad (I)$$

wherein $R_1$ is a $C_6$ to $C_{19}$ hydrocarbyl group, optionally substituted with a hydroxyl or a $C_1$–$C_5$ hydrocarbyl group; and X is ammonium;

wherein no more than 0.5 wt. % of the active ingredient is free fatty acid.

2. The method of claim 1, wherein the composition contains two or more compounds of formula $R_1COO^-X^+$.

3. The method of claim 1, wherein $R_1$ is a $C_7$ to $C_{11}$ hydrocarbyl group.

4. The method of claim 3, wherein the compound of formula (I) is ammonium pelargonate.

5. The method of claim 1, wherein the composition contains two or more salts represented by formula (I) wherein $R_1$ is selected from $C_8$, $C_9$, and $C_{10}$ hydrocarbyl groups.

6. The method of claim 5, wherein one of the salts is ammonium pelargonate.

7. The method of claim 1, wherein the composition further comprises a diluent.

8. The method of claim 7, wherein the diluent is water and the compound of formula (I) is ammonium pelargonate.

9. The method of claim 1, wherein the vegetation is quack grass, buttercup, common cinquefoil, multi flora rose, common yellow woodsorrel, prostrate spurge, poison ivy, poison hemlock, common speedwell, broadleaf plantain, Japanese honeysuckle, dandelion, wild violet, Bermuda grass, nutsedge, wild garlic, knotweed, red sorrel, lambs quarters, pokeweed, carpetweed, crabgrass, buckhorn plantain, nimblewill or common chickweed.

10. A method for the prevention or elimination of undesired vegetation which comprises applying to the vegetation a herbicidally effective amount of an aqueous solution which contains, as the active ingredient, a salt represented by the formula:

$$R_1COO^-X^+ \qquad (I)$$

wherein $R_1$ is a $C_6$ to $C_{19}$ hydrocarbyl group, optionally substituted with a hydroxyl or a $C_1$–$C_5$ hydrocarbyl group; and X is ammonium;

wherein no more than 0.1 wt. % of the active ingredient is free fatty acid.

11. The method of claim 10, wherein the composition contains two or more salts of the formula $R_1COO^-X^+$.

12. The method of claim 10, wherein $R_1$ is a $C_7$ to $C_{11}$ hydrocarbyl group.

13. The method of claim 12, wherein the salt of formula (I) is ammonium pelargonate.

14. The method of claim 10, wherein the composition contains two or more salts represented by formula (I) wherein $R_1$ is selected from $C_8$, $C_9$, and $C_{10}$ hydrocarbyl groups.

15. The method of claim 14, wherein one of the salts is ammonium pelargonate.

16. The method of claim 10, wherein the composition further comprises a diluent.

17. The method of claim 16, wherein the diluent is water and the compound of formula (I) is ammonium pelargonate.

18. The method of claim 10, wherein the vegetation is quack grass, buttercup, common cinquefoil, multi flora rose, common yellow woodsorrel, prostrate spurge, poison ivy, poison hemlock, common speedwell, broadleaf plantain, Japanese honeysuckle, dandelion, wild violet, Bermuda grass, nutsedge, wild garlic, knotweed, red sorrel, lambs quarters, pokeweed, carpetweed, crabgrass, buckhorn plantain, nimblewill or common chickweed.

19. The method of claim 1, wherein the composition contains from about 5 to about 10 percent by weight of the compound of formula (I).

20. The method of claim 1, wherein the composition contains from about 10 to about 15 percent by weight of the compound of formula (I).

* * * * *